US006352860B1

(12) United States Patent
Madsen et al.

(10) Patent No.: US 6,352,860 B1
(45) Date of Patent: Mar. 5, 2002

(54) LIQUID AND SOLID TISSUE MIMICKING MATERIAL FOR ULTRASOUND PHANTOMS AND METHOD OF MAKING THE SAME

(75) Inventors: Ernest L. Madsen; Gary R. Frank, both of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/715,400

(22) Filed: Nov. 17, 2000

(51) Int. Cl.[7] .......................... G01N 29/00; G01N 37/00
(52) U.S. Cl. .......................... 436/8; 73/1.84; 73/866.4; 600/437; 252/408.1; 516/105
(58) Field of Search .......................... 436/8; 252/408.1; 424/9.1, 9.5, 9.51, 9.52; 73/1.84, 1.86, 644, 866.4; 367/13; 516/103, 105; 600/437

(56) References Cited

U.S. PATENT DOCUMENTS

| | | | |
|---|---|---|---|
| 4,277,367 A | 7/1981 | Madsen et al. | 436/8 |
| 4,286,455 A * | 9/1981 | Ophir et al. | 73/1.83 |
| 4,843,866 A | 7/1989 | Madsen et al. | 73/1.86 |
| 5,312,755 A * | 5/1994 | Madsen et al. | 436/8 |
| 5,625,137 A | 4/1997 | Madsen et al. | 73/1.84 |
| 5,902,748 A | 5/1999 | Madsen et al. | 436/8 |
| 6,190,915 B1 * | 2/2001 | Madsen et al. | 436/8 |
| 6,238,343 B1 * | 5/2001 | Madsen et al. | 600/437 |

OTHER PUBLICATIONS

Madsen et al. *Ultrasound in Medicine and Biology* vol. 24, No. 4, pp. 535–542, 1998.*
E.L. Madsen, et al., "System for Determination of Ultrasound Exposure Parameters," Journal of Ultrasound in Medicine, vol. 18, No. 3 (supplement), Mar., 1999, p. S:125.
E.L. Madsen, et al., "System for Determination of Ultrasound Exposure Parameters," copies of slides presented at American Institute of Ultrasound in Medicine Annual Convention, San Antonio, Texas, Mar. 14–17, 1999.

* cited by examiner

Primary Examiner—Maureen M. Wallenhorst
(74) Attorney, Agent, or Firm—Foley & Lardner

(57) ABSTRACT

A tissue mimicking material for ultrasound phantoms has ultrasound speed and attenuation characteristics that are characteristic of human tissue and well suited for use in measuring and calibrating the potential biological effects of ultrasound equipment. The material is formed of an aqueous mixture of large organic water soluble molecules condensed from skim milk with a total solids content in the range of 10% to 30% by weight. The total fat content is less than 1% by weight, with the residual lipid particles of a size sufficiently small to remain in suspension without agglomerating and separating from the mixture over extended periods of time.

26 Claims, 3 Drawing Sheets

US 6,352,860 B1

LIQUID AND SOLID TISSUE MIMICKING MATERIAL FOR ULTRASOUND PHANTOMS AND METHOD OF MAKING THE SAME

This invention was made with United States government support awarded by the following agency: NIH Grant No. GM54377. The United States government has certain rights in this invention.

FIELD OF THE INVENTION

This invention pertains generally to the field of materials which closely mimic the ultrasonic propagation characteristics of human tissue, and particularly to such materials used in ultrasound phantoms for use with ultrasound scanners.

BACKGROUND OF THE INVENTION

Materials which closely mimic the ultrasonic propagation characteristics of human tissue are employed in imaging phantoms and other test objects for use with ultrasound scanners. These phantoms may be used to carry out performance checks on ultrasound scanners. Phantoms may also be used for training or testing student technologists in the operation of ultrasound scanners or the interpretation of ultrasound images produced by such scanners.

Ideally, such material should be capable of mimicking soft human tissue with respect to at least three characteristics: speed of sound, ultrasonic attenuation, and ultrasonic scattering. The speed of sound in the tissue mimicking material should rest in the range from approximately 1460 m/s, characteristic of human fat tissue, to 1640 m/s, characteristic of the human eye's lens. The attenuation coefficient with respect to frequency of the material should lie in the range from approximately 0.4 dB/cm/MHz, characteristic of human fat tissue, to 2.0 dB/cm/MHz, characteristic of human muscle tissue. Additionally, the attenuation coefficient should be approximately proportional to the ultrasonic frequency. In other words, the attenuation coefficient with respect to frequency, or the attenuation coefficient slope, should remain constant for varying ultrasonic frequencies. These characteristics of human tissue should be maintained at all frequencies in the typical range of ultrasonic scanners, from 1–10 MHz. Moreover, the variation of these characteristics within the range of room temperature should be small. Additionally, these materials should be stable in time and invulnerable to reasonable environmental fluctuations. They should also be free of any pockets of air or gas. Furthermore, the bulk properties of the material should be the same throughout the volume of a particular phantom or phantom section.

A tissue mimicking material satisfying the above characteristics was disclosed in U.S. Pat. No. 4,277,367, to Madsen, et al., entitled Phantom Material and Methods, in which both the speed of sound and the ultrasonic attenuation properties could be simultaneously controlled in a mimicking material based on water based gels, such as those derived from animal hides. In one embodiment, ultrasound phantoms embodying the desired features for mimicking soft tissue were prepared from a mixture of gelatin, water, n-propanol and graphite powder, with a preservative. In another embodiment, an oil and gelatin mixture formed the basis of the tissue mimicking material.

Tissue mimicking material is typically used to form the body of an ultrasound scanner phantom. This is accomplished by enclosing the material in a container which is closed by an ultrasound transmitting window cover. The tissue mimicking material is admitted to the container in such a way as to exclude air bubbles from forming in the container. In addition to the tissue mimicking material itself, scattering particles, spaced sufficiently close to each other that an ultrasound scanner is incapable of resolving individual scattering particles, and testing spheres or other targets may be located within the phantom container, suspended in the tissue mimicking material body. Such an ultrasound phantom is useful in evaluating the ability of ultrasound medical diagnostic scanners to resolve target objects of selected sizes located throughout the tissue mimicking material. The objective is for the ultrasound scanner to resolve the testing spheres or other targets from the background material and scattering particles. This type of ultrasound phantom is described in U.S. Pat. No. 4,843,866, to Madsen, et al., entitled Ultrasound Phantom.

U.S. Pat. Nos. 5,625,137 and 5,902,748 to Madsen, et al. disclose a tissue mimicking material with very low acoustic backscatter coefficient that may be in liquid or solid form. A component in both the liquid and solid forms is a filtered aqueous mixture of large organic water soluble molecules and an emulsion of fatty acid esters, which may be based on a combination of milk and water. Hydroxy compounds, such as n-propanol, can be used to control the ultrasonic speed of propagation through the material and a preservative from bacterial invasion can also be included. The use of scattering particles allows a very broad range of relative backscatter levels to be achieved.

In an effort to limit patient exposure to ultrasound, the Food and Drug Administration (FDA) and the American Institute of Ultrasound in Medicine have made recommendations to ultrasound equipment manufacturers that values of two parameters, which are relevant to potential biological effects, be available to clinical users. One parameter is the thermal index (TI), the value of which is a predictor for temperature rise of tissue in an ultrasound beam. The other recognized potential mechanism of biological damage involves cavitation, and the likelihood of patient injury due to cavitation is thought to increase with the value of the parameter referred to as the mechanical index (MI). The definitions and models for the TI and MI are detailed in a standard produced by a joint committee of the American Institute of Ultrasound in Medicine (AIUM) and the National Electrical Manufacturers Association (NEMA).

In acoustic output quantification, a hydrophone is typically used in a water tank to record the temporal acoustic pressure of a propagating wave. The most extreme rarefactional pressure, $p_r$, is used for calculating MI, and the pulse intensity integral, PII, is used for calculating the temporal average intensity. The MI and the temporal average intensity are subject to restrictions imposed by the FDA. The temporal average intensity is also used in calculating TI.

According to the presently applicable standards, the water-measured pressures and intensities are made to model the attenuation effects of tissue through the application of a derating factor. Derating is applied to any waveform by multiplying all acoustic pressures, p(t) (at time t) by a factor $e^{-\alpha f_0 z}$ where $\alpha$=0.3 dB/cm-MHz=0.0345 nepers/cm-MHz is the attenuation coefficient slope, $f_0$ is the center frequency of the pulse, and z is the distance from the transducer to the receiver. Use of the deration process assumes that the propagation of the sound pulse in water or in tissue is linear. However, it is well known that most diagnostic ultrasound systems commonly emit pulses which are nonlinear for propagation in both water and tissue. Generation of pulse nonlinearities in the water is a concern because the derating process assumes linear propagation and a result can be significant underestimation of intensity. It is not known to what extent such nonlinearities occur in tissue although it is thought that most tissues are less subject to such an effect than water.

There are two approaches to replacing the presently used water-deration method of measurement with more acceptable methods. One is theoretical, viz, to extend the deration method to account for nonlinear propagation in both water and a hypothetical tissue-mimicking material using the Khokhlov-Zabolotskaya-Kuznetsov (KZK) equation. The other approach for accurately determining exposure parameters is direct experimental measurement using a medium which adequately mimics tissue in the relevant ultrasonic parameters, viz, propagation speed, attenuation and nonlinear propagation. The liquid tissue mimicking material disclosed in U.S. Pat. Nos. 5,625,137 and 5,902,748 may be utilized for this purpose. Tests of the accuracy of the water-derating procedure have been made employing a tissue-mimicking liquid as described in U.S. Pat. Nos. 5,625,137 and 5,902,748 with properties recommended by the American Institute of Ultrasound in Medicine (AIUM) and having a B/A value typical of soft tissue. The peak PII found in the tissue-mimicking liquid is more than twice that measured under identical conditions in water (and derated). Another example is rarefactional pressures measured in such tissue mimicking liquid and in water (with derating), where the peak value in the tissue mimicking liquid is found to be about twice the peak water-derated value. However, there are two disadvantages in the use of this liquid material and the open tank measurement method. Firstly, material made with condensed whole milk has the long term (a few months) disadvantage that lipid particles collect at upper surfaces, thus compromising the spatial uniformity of ultrasonic properties. Secondly, if this liquid is left for long periods (a few months) exposed to air, desiccation and clumping occur. If condensed whole milk containing either thimerosal or 1-(cis-3-chlorallyl)-3,5,7-triaza-1-azonia adamantane chloride as a preservative is stored in a container so that it is isolated from air, the clumping mentioned does not occur. Sedimentation of the lipids cannot be avoided, however, and to assure uniformity of properties after storage of the tissue mimicking liquid for weeks or months, the liquid must be vigorously agitated before the tests can be performed.

SUMMARY OF THE INVENTION

In accordance with the invention, a tissue mimicking material for ultrasound phantoms is provided that has a speed of sound and ultrasound attenuation that are characteristic of human tissue, and that is well suited to be used for measuring and calibrating the potential biological effects of ultrasound equipment. The material provides more realistic tests of the biological effects of ultrasound equipment than conventional water based tests. For use in testing biological effects of ultrasound equipment, the tissue mimicking material of the invention is provided in a liquid form having preferred characteristics at normal room temperature of a suitable propagation speed characteristic of human tissue and a constant attenuation coefficient slope. The liquid tissue mimicking material is stable in its characteristics over extended periods of time, allowing the material to be utilized repeatedly over long periods of time to provide comparative tests of ultrasound equipment, including periodic tests of a particular medical ultrasound unit to determine changes in the unit's characteristics over time.

The liquid tissue mimicking material of the invention allows ultrasound scanner beam properties to be determined at arbitrary positions by immersing movable detectors or reflectors at various positions in the container of the phantom containing the liquid tissue mimicking material. Further, phantom test objects may be refilled with materials mimicking ultrasonically different tissues.

The liquid tissue mimicking material of the invention is formed of an ultra-filtered aqueous mixture of large organic water soluble molecules in water that is condensed from milk. A preservative is generally included in the mixture to inhibit bacterial invasion. The material is formed of ultra-filtered skim milk in which the fat content has been reduced below 1% while total solids are in the range of 10% to 30%. For use as a material for testing the biological effects of ultrasound equipment, the tissue mimicking material is preferably concentrated such that the speed of sound in the material at 22° C. (typical room temperature) is in the range of 1460 m/s to 1640 m/s, preferably at approximately 1540 m/s, with an attenuation coefficient slope of about 0.3 dB/cm/MHz. The total fat content of the ultra-filtered milk forming the material is preferably less than 0.6%, with total solids preferably about 14% by weight of the material. The total fat content is selected to be sufficiently low and the size of the remaining lipid particles sufficiently small that essentially no separation of lipids from the remaining water and other solid materials occurs over substantial periods of time, many months to a year or more, so that the functional ultrasound characteristics of the tissue mimicking material do not change over time. The maximum diameter of the lipid particles remaining after ultrafiltration is sufficiently small so that the lipid particles do not agglomerate, and the lipid particles remain in suspension over extended periods of time. Preferably, the average lipid particle diameter is less than about 0.02 to 0.03 micrometers. It is believed that by maintaining the total lipids content below about 1%, and by maintaining the remaining lipid particles below a size of 0.02 to 0.03 micrometers in diameter, the lipid particles remain in suspension and do not agglomerate into larger particles which can float by gravity to the surface of the tissue mimicking material over long enough periods of time.

The tissue mimicking material of the present invention may also be embodied in a form suitable for use as a phantom for carrying out performance evaluations on ultrasound scanners. In such phantoms, the tissue mimicking material of the invention may also be in solid form in which a pure gel forming material is included to form an elastic solid tissue mimicking material. Solid scatterers and/or test objects may be added to the solid type of tissue mimicking material. For use in testing the general performance characteristics of ultrasound scanners, the solid tissue mimicking material is preferably concentrated such that the propagation speed is maintained at about 1540 m/s±5 m/s with an attenuation coefficient slope of about 0.5 dB/cm/MHz.

Further objects, features and advantages of the invention will be apparent from the following detailed description when taken in conjunction with the accompanying drawings.

DETAILED DESCRIPTION OF THE INVENTION

Figure 1:
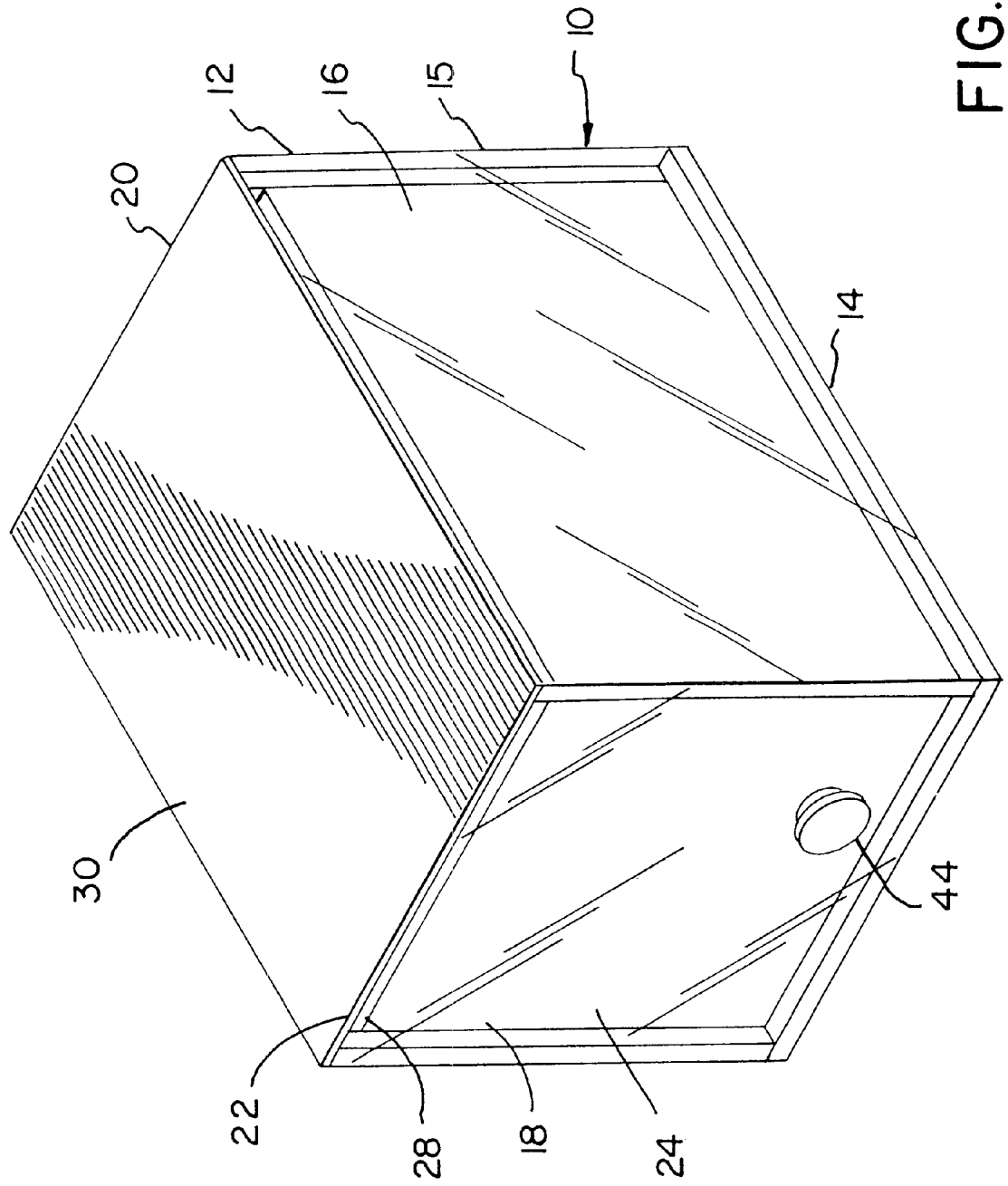
FIG. 1 is a perspective view of an ultrasound phantom containing the tissue mimicking material of the present invention which is suited for use in testing the ultrasonic performance characteristics of an ultrasound scanner.

The tissue mimicking material of the present invention is an ultrafiltered aqueous mixture of large organic water soluble molecules in water with a low concentration residue emulsion of fatty acid esters (lipids) that is obtained by the condensation (e.g., by ultrafiltration) of milk and the removal of lipids from the concentrated milk to below a level at which the lipids will separate from the other material over time. A preservative against bacterial invasion is also preferably included in the material. An organic hydroxy compound may be included in the material for purposes of controlling the ultrasonic speed of propagation through the material. An example of the hydroxy compound is n-propanol and an example of a preferred preservative is thimerosal.

The present invention avoids the problem of separation of lipids from liquid milk-based tissue mimicking material by reducing the concentration of lipids to below 1% by weight of the material and preferably to 0.6% or less. It is also preferred that the size of the lipid particles be reduced to a diameter at which the lipid particles do not agglomerate and separate out by gravity, typically in the range of 0.02 to 0.03 micrometers or less. The concentration of total solids in the concentrated milk, which comprises primarily the water soluble components, is at least 10% by weight and preferably in the range of 10% to 30%, for example at 14%. The solids components of the material are selected to provide the desired propagation speed and attenuation coefficient slope. For example, for a liquid tissue mimicking material to be utilized for testing the biological effects of an ultrasound scanner, the propagation speed is preferably in the range of about 1460 to 1640 m/s, with a substantially constant attenuation slope. Exemplary preferred characteristics of the material for such purposes are a propagation speed of 1540 m/s±5 m/s and an attenuation coefficient slope of 0.3 dB/cm/MHz at 22° C. For use of the tissue mimicking material in a phantom utilized to simulate human tissue for testing the imaging characteristics of ultrasound scanners, similar conditions are preferred. Exemplary preferred characteristics of the tissue mimicking material for such purposes include a propagation speed of 1540 m/s±5 m/s and an attenuation coefficient slope of 0.5 dB/cm/MHz. In accordance with the invention, selection of the attenuation coefficient slope can be obtained by processing the tissue mimicking material to selectively remove or add components which affect the attenuation coefficient slope.

The following examples are illustrative of the invention but are not to be considered as limiting the invention to the specific examples provided herein.

A tissue mimicking material suitable for testing the biological effects of ultrasound scanners was produced in the following manner. A sample of skim milk that had been concentrated by a factor of 3 by ultra-filtration was obtained from Diehl, Inc. of Defiance, Ohio. The skim milk was concentrated by Diehl, Inc. utilizing an ultrafiltration unit with a 10,000 molecular-weight cut-off. Thus, water and other molecules of molecular weight less than 10,000 were removed by this ultrafiltration technique. The fat content of the sample obtained from Diehl, Inc. was about 1% by weight, which is about three times the usual fat content in normal concentration skim milk. One gram per liter of the preservative 1-(cis-3-chloroallyl)-3,5,7-triaza-1-azonia-adamantane chloride, was well mixed and dissolved in the sample. The sample was maintained in a sealed bottle for about two weeks, during which time a lipid layer formed at the top of the liquid. A catheter tube on a syringe was inserted through the lipid layer, and the liquid under the liquid layer material was withdrawn through the catheter from the bottle in a quantity sufficient to make a test cylinder for measuring ultrasonic properties. The properties, measured at 22° C. were as follows: ultrasound propagation speed=1539.7±0.5 m/s; attenuation coefficient=1.36±0.5 at 4.5 MHz and 2.58±0.5 dB/cm/MHz at 8.0 MHz.

The sample was maintained in the test cylinder for five weeks. At the end of that time, the sample was examined and no white lipid layer was observed at the top of the sample, indicating that no more lipid particles were separating by gravitation effect. Using care not to mix by agitation or rotation of the sample, it was placed in apparatus for measuring ultrasonic properties. The following results were obtained: ultrasound propagation speed=1540.2±0.5 m/s; attenuation coefficient=1.35±0.5 at 4.5 MHz and 2.5±0.5 dB/cm/MHz at 8.0 MHz. The values for propagation speed and attenuation coefficient were thus essentially identical to the values measured in the sample 41 days earlier, verifying that the material was not changing over this period of time in ultrasonic properties due to gravitational sedimentation.

Tests were performed on three samples prepared in a manner similar to that described above to determine total fat content and total solids content. The average fat content over the three samples was 0.33% by weight and total solids content averaged over the three samples was 15.13% by weight. Fat content was determined via Procedure No. 989.05 (Section 33.2.26) and total solids via Procedure No. 925.23 (Section 33.2.09) in the "Official Methods of Analysis of the Association of Official Analytical Chemists," $16^{th}$ edition, $5^{th}$ revision, 1999, AOAC International, Gaithersburg, Md.

It is generally important that the pH of the tissue mimicking material be kept between 6.6 and 7.0. If the pH is significantly lower, e.g., 6.1, jelling of proteins can occur making the material no longer liquid. The pH may be raised to the desired range utilizing a small amount of NaOH solution.

The maximum size of the remaining lipid particles was calculated based on the characteristics of the container in which the tissue mimicking material is held. The calculation may be done assuming the exponential variation in concentration with depth, that is, concentration at a height z=concentration at height 0 times exp[upward buoyant force on particle minus gravitational force] times z divided by kT, where k Boltzmann's constant and T is the room temperature in Kelvins. For example, for a container containing 50 cm height of liquid, in order that the concentration of the fat particles (specific gravity 0.92) in the liquid tissue mimicking material (specific gravity 1.06) at the top be no more than e (about 2.72) times the concentration at the bottom, the maximum average diameter value is found to be about 0.02 to 0.03 micrometers.

In another example of the present invention, tissue mimicking material was prepared which has an appropriate attenuation coefficient slope for use of the material as a low echo liquid in phantoms for testing the imaging performance of diagnostic ultrasound scanners. For such applications, the attenuation coefficient slope generally must be about 0.5 dB/cm/MHz with a propagation speed of 1540±5 m/s at room temperature (20°–22° C.). Such material is produced by successive rinsing with water of highly concentrated skim milk to remove sufficient salts and lactose such that the speed may be maintained at 1540 m/s (the canonical speed required by industry in ultrasound phantoms), while raising the attenuation coefficient to 0.5 dB/cm/MHz, the recommended attenuation coefficient slope for ultrasound phantoms. Such material may be prepared from skim milk available from Diehl, Inc. that is concentrated by a factor of six from the original skim milk, with the sample allowed to stand to separate excess lipids by gravity separation followed by withdrawal of the low fat portion of the liquid in the manner described above to form the tissue mimicking material. A resulting fat content for this material is about 0.5%. The rinsing of such material with pure water can be carried out to lower the propagation speed inasmuch as propagation speed increases linearly with salt, lactose and protein concentrations. The resulting tissue mimicking material had a propagation speed of 1540 m/s and an attenuation coefficient slope of 0.5 dB/cm/MHz, and has excellent properties for use as a very low scatter liquid tissue-mimicking material, and may be used in various solid phantoms or as a liquid to fill a tank for general measurement purposes.

Highly concentrated milk for use in forming the tissue mimicking material of the present invention may be obtained commercially as discussed above, and may be produced by the ultrafiltration of skim milk utilizing various apparatus and techniques. For example, skim milk may be concentrated utilizing an ultrafiltration system manufactured by the A/G Technology Corporation, of Needham, Mass., sold under the name FlexStand Benchtop System with Rotary Lobe Pump (Part no. FS-2RLP). This system will process 5 to 100 liters per run. A nominal 10,000 molecular weight cut-off ultrafilter (A/G Technology Corporation Model No. UFP-10-C55) may be installed on the FlexStand unit. In use, the pump moves a liquid to be concentrated through many parallel small diameter tubes that extend the length of the ultrafilter cartridge. The liquid to be concentrated passes through the insides of these tubes. The gauge pressure is preferably kept at about 15 psi on the ends of the tube where the liquid enters and 7 psi at the exit end. The pressure in the region outside of the tubes in the cartridge is atmospheric pressure. Water, inorganic salts, and small organic molecules, such as lactic acid, pass through the membrane and constitute the permeate, which is discarded.

The liquid form of the tissue mimicking material of the present invention can be used to allow the beam properties of ultrasound medical equipment to be determined at arbitrary positions by immersing movable ultrasound detectors or reflectors in the liquid tissue mimicking material held in a reclosable container. If it is undesirable for the ultrasound detector to be immersed in liquid other than pure water, then the liquid tissue-mimicking material can be enclosed in a flexible bag surrounded by water. The flexibility of the bag can be utilized to make the distance between the source and the detector continuously variable. Additionally, test object phantom containers can be refilled with liquid material which mimics ultrasonically different parenchymal tissues.

A solid tissue mimicking material in accordance with the present invention may be formed as described in U.S. Pat. Nos. 5,625,137 and 5,902,748, which are incorporated herein by reference . Such material contains the same components as the liquid form, with a very pure gel-forming material such as gelatin, polyacrylamide gel, or agarose included to form a solid material. A preferred gel-forming material is agarose. The high purity gel-forming material performs the function of maintaining a solid form with the liquid tissue mimicking components held therein without substantial settling or diffusion. This solid and stable gel structure allows complex phantoms to be constructed containing, e.g., simulated tumors with different backscatter characteristics than the surrounding phantom body material, as described in more detail below.

An ultrasound scanner phantom incorporating the solid tissue mimicking material of the present invention is shown generally at 10 in FIG. 1. The ultrasound phantom 10 includes a container 12 having a bottom 14 and walls 15. Preferably the walls 15 include opposed faces 16, and opposed ends 18. Taken together, the bottom, faces, and ends 14, 16, and 18 form a hollow, box-like container structure. Margins of the walls 15 remote from the bottom 14 define a window 20. The window 20 is closed with an ultrasound-transmitting window cover 22. The window cover 22 may be made of any cohesive ultrasound transmitting material of suitable physical durability such as a thin sheet of polyurethane or saran or of plastic coated aluminum film.

The ultrasound phantom 10 further includes a body 24 of the tissue mimicking material of the present invention. This material substantially fills the container 12 up to the level of the window 20, except as shall be discussed below. The phantom body 24 includes the tissue mimicking material of the present invention 26. As discussed above, the material 26 has attenuation and ultrasonic speed characteristics of human tissue combined with a very low ultrasonic backscatter coefficient. Solid scattering particles may be added to the solid form of phantom body 24 such that their presence increases the backscatter coefficient of the tissue mimicking material 26 to a selected level. The liquid version of the material is not capable of maintaining a uniform suspension of solid scattering particles because of the great difficulty of precisely matching specific gravities of liquid and solid scatterers. To be effective, a scattering particle must be large enough so that measurable ultrasonic scatter occurs and small enough and sufficiently closely spaced that the texture pattern displayed by the ultrasound scanner being tested does not represent resolution of individual scattering particles. Any material that differs from the tissue mimicking material 26 in specific gravity and/or ultrasonic speed is capable of causing scatter. Glass beads have been found acceptable for use as scattering particles, with the diameters of the glass beads being not less than 40 microns and not greater than 100 microns. Preferably these solid scattering particles may be included in the solid type tissue mimicking material of the present invention by adding 45–53 micron diameter glass beads at a concentration of a few grams per liter to the tissue mimicking material, prior to cooling the mixture and before congealing. Allowing the phantom to rotate overnight, to assure congealing without gravitational sedimentation, is particularly important when such scatterers have been added and sedimentation of the glass beads might occur.

The tissue mimicking material of the present invention contains water and is subject to drying by escape of the water to the atmosphere. This can result in changes in acoustic properties that make the material a less effective tissue mimicker. Consequently, the container 12 must be liquid tight and preferably also water vapor tight. The window cover 22 must include means for reducing water transfer therethrough. To this end, the window cover 22 may be made of a flexible plastic material that does not readily transmit water vapor. A plastic coated aluminum film may be used. An alternative means for reducing water transfer through the window cover 22 includes a layer 28 of an oil-based gel that completely closes the window 20 and which is covered with a thin and flexible plastic sheet 30 that serves to form and protect the surface of the layer 28 of oil-based gel.

In practice, the bottom 14, faces 16, and ends 18 may be molded as a unit or formed of flat pieces of plastic or other material and be glued or otherwise joined so as to constitute the container 12. If the window cover 22 is to include the layer of oil-based gel, the plastic sheet 30 may first be glued or otherwise attached to the container 12 so as to close the window 20 in liquid-tight relation. At least one of the bottom 14, faces 16, or ends 18 includes a filling hole, shown at 32 and located in an end 18 of the ultrasound phantom 10 shown in FIG. 1 and FIG. 2. The layer 28 of oil-based gel may then be created by inserting through the filling hole 32 a sufficient quantity of the oil-based gel to make the layer 28, the oil-based gel so inserted being in molten form. With the container 12 oriented so that the window 20 is downward most, the molten oil-based gel may then be allowed to cool and solidify. The exact thickness of the layer 28 is not critical. The container may be filled as described in the aforesaid U.S. Pat. Nos. 5,625,137 and 5,902,748.

The phantom body 24 may contain, in addition to the solid tissue mimicking material 26, testing spheres 46. This important version of the phantom may be referred to as a "lesion detectability phantom." In this type of phantom, it is necessary that the ultrasonic speed of propagation and attenuation coefficient slope be the same everywhere in the phantom body 26 with the only variable being the backscatter coefficient over the small, lesion-like, spherical target volumes.

The testing spheres 46 may be made of the tissue mimicking material of the present invention, and may, therefore, have the same ultrasonic speed and attenuation characteristics of the rest of the material 26 in the phantom body 24. However, the testing spheres 46 must then have a backscatter coefficient or other characteristics different from that of the other material 26. The testing spheres 46, therefore, may most conveniently be made of the tissue mimicking material of the present invention with a different concentration of scattering particles, such as glass beads, than in the body material 26.

If the glass bead concentration is the same in the test lesions 46 as in the tissue mimicking material surrounding them 26, then the lesions are not detectable in ultrasound images because there is no backscatter contrast. Contrast is attained by having a different concentration of glass beads in the lesions than in their surroundings. The concentration of 40 micrometer diameter glass beads in the surroundings must be about 8 grams per liter so that the backscatter is representative of commonly scanned organ parenchymae such as liver.

Figure 2:
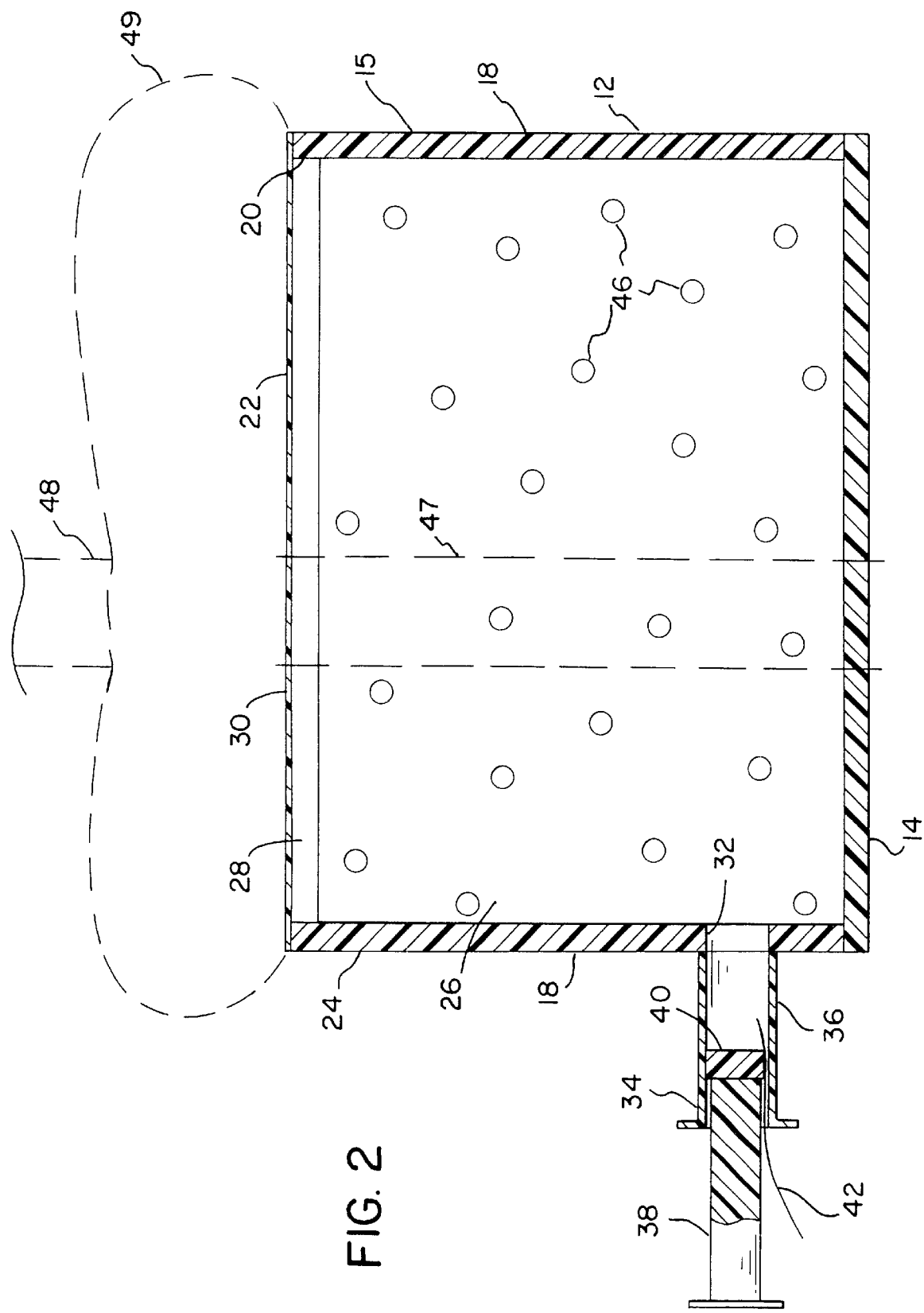
FIG. 2 is a cross-sectional view of an ultrasound phantom similar to that of FIG. 1 showing testing spheres suspended through solid tissue mimicking material enclosed in the phantom.

The diameter of the testing spheres is selected to be of a size appropriate for testing the resolution abilities of an ultrasound scanner having an ultrasound scanning head, such as that shown in FIG. 2 at 48. The ultrasound scanning head 48 may either be directly applied to the window cover 22, or, as is shown in FIG. 2, may be equipped with a water bag 49 or any of the other spacers or surface conformation arrangements commonly used with diagnostic and other ultrasound scanning heads. As is well known to those skilled in the art, an ultrasound scanning head may be used to scan a space below it commonly referred to as a slice, indicated in FIG. 2 at 47. Any ultrasound scanning head has a zone within the slice being scanned within which it achieves resolution of objects of a given size and acoustical characteristics. No matter what size of testing sphere 46 is employed, it will be apparent that the phantom 10 may be used to demonstrate the ability of the ultrasound scanning head 48 to resolve spheres of that size at any given location within the slice 47. Furthermore, the phantom 10 can be used to demonstrate the ability of the ultrasound scanner to so detect the testing spheres 46 when they differ from the tissue mimicking body material 26 in backscatter coefficient or other ultrasound acoustical property to any selected extent. The advantages of unpredictable locations of the testing spheres 46 within the phantom body 24 are described in U.S. Pat. No. 4,843,866, incorporated herein by reference.

For use as the window cover 30, a multi-layer film comprising a layer of metal foil between layers of plastic is generally preferred because the plastic layers protect the metal from physical abrasion, oxidation and corrosion. An appropriate multi-layer film comprising a metal layer adhered to a plastic layer may be utilized. The metal layer preferably is not susceptible to corrosion when in contact with the tissue mimicking material. Such multi-layer films can include, for example, a layer of silver covered by a layer of inconel metal (a nickel/chromium alloy) both sputtered into a polyester film of 25 to 75 $\mu$m thickness (e.g., from Innovative Specialty Films, Inc.). The inconel metal is resistant to corrosion. The metal surface may be directly adhered (e.g., with epoxy) to the margins of the container walls defining the window(s). Multi-layer films incorporating other plastic materials may also be utilized. An example is a multi-layer film comprised of a layer of aluminum foil between layers of polyester, which is well suited to be adhered with a water resistant glue.

Figure 3:
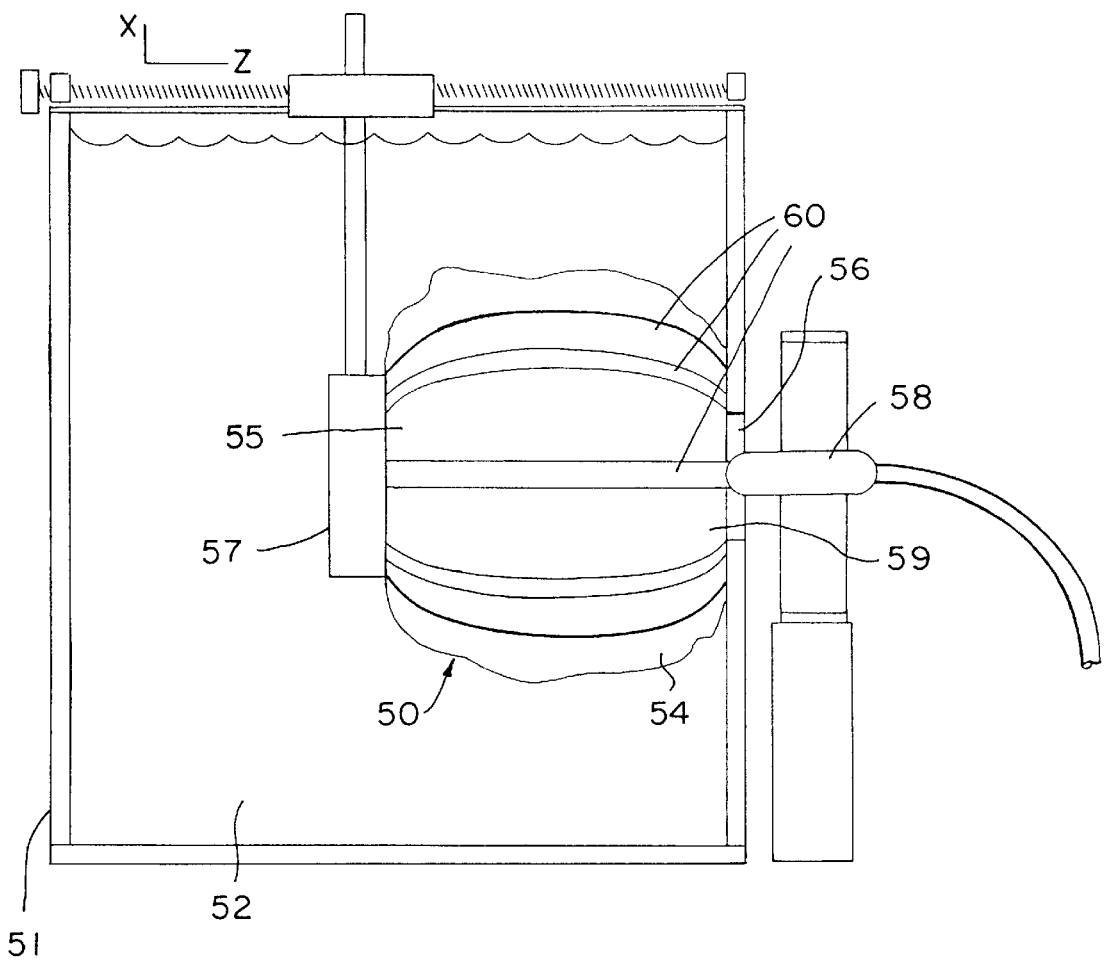
FIG. 3 is a simplified view of a phantom formed of flexible plastic containing the tissue mimicking material, with the phantom immersed in a water bath within a container.

With reference to FIG. 3, a tissue mimicking phantom 50 in accordance with the invention is shown mounted within an enclosure 51 for holding a liquid (typically water) bath 52. The ultrasound phantom 50 comprises a flexible sack container 54 which surrounds and encloses a tissue mimicking material 55 within it, which may be solid or liquid. The structure of FIG. 3 is particularly useful with a water based liquid tissue mimicking material within the sack 54 since it allows coupling of ultrasound through the liquid material to a hydrophone 57, transmitted from an ultrasound transducer 58 through an opening 56 in a wall of the container 51 to the phantom 50. If desired, the hydrophone 57 may be mounted on a commercial x-y-z translator for positioning of the hydrophone. The flexible sack 54 is formed of a plastic coated metal foil material 59, particularly the preferred multi-layer film material as described above, which may be heat sealed utilizing the heat sealable Scotch-Pak® layer to provide the enclosed sack 54. Flexible plastic reinforcing strips 60 (e.g., 0.7 mm thick flexible polycarbonate strips attached to the walls of the enclosure 51) within the sack 54 may be used to provide structural support for the container sack 54. Because the multi-layer film 59 forming the walls of the container 54 is essentially impervious to transmission of water therethrough, the phantom 50 may be submerged in the water bath without transmission of water through the multi-layer film material 59 which, if it occurred, would change the characteristics of the tissue mimicking material within the container. The phantom 50 may utilize a liquid tissue mimicking material as described above. In the phantom testing system of FIG. 3, the opening 56 into the enclosure 51 for the bath may be closed with a multi-layer film of the same type as utilized for forming the walls of the phantom 50, or portions of the sack 54 may be sealed to the areas of the inner wall of the container 51 around the opening 56 to close off the opening.

The ultrasound phantoms described above are examples of many embodiments of ultrasound phantoms which may incorporate the tissue mimicking material of the present invention. Many other materials, arrangements of parts, and modes of assembly are possible.

It is understood that the present invention is not limited to the particular embodiments or processes described herein for illustration, but embraces all such modified forms thereof as come within the scope of the following claims.

What is claimed is:

1. An ultrasound tissue mimicking material comprising:
an aqueous mixture of large organic water soluble molecules in water that is condensed from skim milk, the mixture having a total solids content in the range of 10% to 30% by weight, a total fat content less than 1% by weight, and a quantity of lipid particles having a size which remain in suspension without agglomeration and separation by gravity from the mixture, wherein the total solids content is selected to provide a propagation speed in the range of the propagation speeds in human tissue and a substantially constant ultrasonic attenuation coefficient slope.

2. The tissue mimicking material of claim 1 wherein the total fat content is less than about 0.6% by weight of the mixture.

3. The tissue mimicking material of claim 2 wherein the total solids content is about 14% by weight of the mixture.

4. The tissue mimicking material of claim 1 wherein the total solids content is selected to provide a propagation speed in the range of about 1460 m/s to 1640 m/s.

5. The tissue mimicking material of claim 1 wherein the total solids content is selected to provide a propagation speed of about 1540 m/s±5 m/s and an ultrasonic attenuation coefficient slope of about 0.3 dB/cm/MHz.

6. The tissue mimicking material of claim 1 wherein an average lipid particle diameter is about 0.03 µm or less.

7. The tissue mimicking material of claim 1 wherein the mixture includes a preservative.

8. The tissue mimicking material of claim 7 wherein the preservative is selected from the group consisting of thimerosal and 1-(cis-3-chlorallyl)-3,5,7-triaza-1-azonia adamantane chloride.

9. The tissue mimicking material of claim 1 wherein the pH of the mixture is in the range of 6.7 to 7.2.

10. The tissue mimicking material of claim 1 wherein the total solids content is selected to provide a substantially constant ultrasonic attenuation coefficient slope of about 0.5 dB/cm/MHz.

11. The tissue mimicking material of claim 1 additionally comprising a gel-forming material mixed with the aqueous mixture.

12. An ultrasound phantom comprising:
(a) an ultrasound phantom container;
(b) an aqueous mixture of large organic water soluble molecules in water that is condensed from skim milk in the ultrasound phantom container, the mixture having a total solids content in the range of 10% to 30% by weight, a total fat content less than 1% by weight, and a quantity of lipid particles having a size which remain in suspension without agglomeration and separation by gravity from the mixture, wherein the total solids content is selected to provide a propagation speed in the range of the propagation speeds in human tissue and a substantially constant ultrasonic attenuation coefficient slope.

13. The ultrasound phantom of claim 12 wherein the total fat content is less than about 0.6% by weight of the mixture.

14. The ultrasound phantom of claim 13 wherein the total solids content is about 14% by weight of the mixture.

15. The ultrasound phantom of claim 12 wherein the total solids content is selected to provide a propagation speed in the range of about 1460 m/s to 1640 m/s.

16. The ultrasound phantom of claim 12 wherein the total solids content is selected to provide a propagation speed of about 1540 m/s±5 m/s and an ultrasonic attenuation coefficient slope of about 0.3 dB/cm/MHz.

17. The ultrasound phantom of claim 12 wherein an average lipid particle diameter is about 0.03 µm or less.

18. The ultrasound phantom of claim 12 wherein the mixture includes a preservative.

19. The ultrasound phantom of claim 18 wherein the preservative is selected from the group consisting of thimerosal and 1-(cis-3-chlorallyl)-3,5,7-triaza-1-azonia adamantane chloride.

20. The ultrasound phantom of claim 12 wherein the pH of the mixture is in the range of 6.7 to 7.2.

21. The ultrasound phantom of claim 12 wherein the total solids content is selected to provide a substantially constant ultrasonic attenuation coefficient slope of about 0.5 dB/cm/MHz.

22. The ultrasound phantom of claim 12 additionally comprising a gel-forming material mixed with the aqueous mixture.

23. A method of producing an improved tissue mimicking material comprising:
(a) ultra-filtering skim milk to provide a concentrated mixture having a total solids content in the range of 10% to 30% by weight;
(b) storing the concentrated mixture for a period of time sufficient for separation of lipids from the mixture by gravity into a lipid layer at the top of the mixture; and
(c) drawing out material beneath the lipid layer to provide a concentrated liquid tissue mimicking mixture having a total fat content of less than 1% by weight with lipid particles therein having a size which remain in suspension without agglomerating and separating from the mixture over long periods of time.

24. The method of claim 23 wherein the mixture is maintained in storage for a period of time sufficient to separate a sufficient amount of lipids by gravity from the remaining mixture under the lipid layer such that the fat content of the liquid tissue mimicking material drawn from beneath the lipid layer is less than 0.6% by weight of the mixture.

25. The method of claim 23 further including the step of rinsing the concentrated liquid tissue mimicking mixture to adjust the concentration of salts, lactose and proteins in the mixture in accordance with a desired propagation speed and ultrasonic attenuation coefficient slope.

26. The method of claim 23 further including mixing a preservative with the concentrated mixture before storing the concentrated mixture.

* * * * *